(12) United States Patent
Boberg et al.

(10) Patent No.: US 6,402,729 B1
(45) Date of Patent: Jun. 11, 2002

(54) DISPOSABLE ABSORBENT ARTICLE WITH HIGH COLLECTION CAPACITY

(75) Inventors: Fredrik Boberg, Alingsås; Carina Hedlund, Kungsbacka; Kent Hermansson, Västra Frölunda; Lennart Nilsson, Skärhamn, all of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/508,600
(22) PCT Filed: Sep. 21, 1998
(86) PCT No.: PCT/SE98/01684
§ 371 (c)(1),
(2), (4) Date: Mar. 14, 2000
(87) PCT Pub. No.: WO99/16398
PCT Pub. Date: Apr. 8, 1999

(30) Foreign Application Priority Data

Sep. 30, 1997 (SE) ................................................ 9703535

(51) Int. Cl.⁷ .................................................. A61F 13/15
(52) U.S. Cl. .......................... 604/385.28; 604/385.26; 604/385.27; 604/385.24
(58) Field of Search ........................... 604/378, 385.05, 604/385.19, 385.26, 385.28, 385.24, 385.27

(56) References Cited

U.S. PATENT DOCUMENTS 5,576,091 A * 11/1996 Zajaczkowski et al. ..... 428/192
5,817,086 A * 10/1998 Kling ...................... 604/385.2
6,152,907 A * 11/2000 Widlund et al. ....... 604/385.08

* cited by examiner

Primary Examiner—John G. Weiss
Assistant Examiner—Jacqueline Stephens
(74) Attorney, Agent, or Firm—Burns, Doane, Swecker & Mathis, L.L.P.

(57) ABSTRACT

An absorbent article having two side edges (9, 10) and two end edges (11, 12), and comprising a liquid-permeable cover layer (2), a liquid-impermeable cover layer (3), and an absorption body (4) enclosed between the two cover layers (2, 3). The article further comprises a barrier layer (15) arranged outside the liquid-permeable cover layer (2). At least one elastic member (22, 23) is arranged with prestressing in direct contact with the absorption body (4) and extends in an arched curve across the absorption body (4) between the side edges (9, 10). The barrier layer (15) partly covers the liquid-permeable cover layer and is anchored in the liquid-permeable cover layer (2) only within areas of the barrier layer (15) which are situated along the edges (9–12) of the article. At least one elastic member (21) is arranged in direct connection with the barrier layer (15), as a result of which the elastic member (21) cooperates with the elastic member (22, 23) arranged in contact with the absorption body (4) so as to form a constantly basin-shaped space (26) between the barrier layer (15) and the liquid-permeable cover layer (2).

16 Claims, 4 Drawing Sheets

DISPOSABLE ABSORBENT ARTICLE WITH HIGH COLLECTION CAPACITY

TECHNICAL FIELD

The present invention relates to an absorbent article, such as a diaper for the incontinent. Such an article comprises an absorption body, which is enclosed between a liquid-permeable cover layer and a liquid-impermeable cover layer. The absorbent article also has a barrier layer arranged on the outside of the liquid-permeable cover layer, and also elastic members for shaping the absorbent article.

RELATED ART

It is previously known to provide a liquid-absorbing article, such as a diaper, with elastic members. The elastic members in this case generally have two main functions. On the one hand, they are used to shape the absorbent article in order to obtain a good fit of the article to a user's body shape, and, on the other hand, elastic members are used to create different types of leakage barriers. For example, most diapers are provided with elastic members along the side edges, as a result of which elastic and leakage-tight leg bands are obtained when the diaper is placed on the user. It is also possible to create liquid-collecting cups and pockets and raised barriers by arranging elastic members on an absorbent article.

Since diapers with leg elastic, for example of the type described in U.S. Pat. No. 3,860,003, came into general use during the 1970s, a very large number of patent applications concerning elastic for diapers have been filed all around the world.

One problem which is particularly associated with absorbent articles intended for incontinent adults is that of leakage due to large amounts of liquid being passed during a short period of time. It can therefore happen that not all the liquid has time to penetrate into the absorbent article, but instead flows out across the surface of the article and causes leakage. Leakage can also occur in connection with children's diapers, on account of the fact that a large amount of liquid impacts the article during a short time. A particular concern with babies diapers is the leakage of excrement. Since babies often have very runny excrement, this behaves as a liquid and can easily run out over the edge of the diaper. Such leakage of excrement is particularly unpleasant, and the stains which are left on soiled clothes and bed-linen are very difficult to wash off.

It has therefore been proposed to use elastic members to create liquid-receiving cup-shaped or basin-shaped spaces in absorbent articles. Such a liquid-receiving space serves as a reservoir in which the liquid is held until it has had time to be absorbed into the absorbent article.

Patent Specification SE-C2 502 818 thus describes a liquid-absorbing article intended for disposal after use, such as a diaper, a sanitary towel or the like. The described article has a generally elongate shape and comprises an absorption body and a cover, enclosing the absorption body, with a liquid-permeable inner layer and an outer layer, and also contracting elastic members arranged in connection with at least one layer.

The cover layer on which the elastic members are arranged is connected to the inside or outside of the absorption body. The elastic members extend with an essentially continuously curved portion across an area of the absorption body. By means of the elastic members being adapted to contract, and by means of the fact that they are connected to one of the cover layers, they exert a contracting force on the cover layer in a direction towards the centre of curvature of the elastic members. The contracting force is additionally transmitted to and taken up by the absorption body. For this purpose, the elastic members are arranged with such pre-stressing that the article is deformed so that a basin wall, essentially transverse to the plane of the article, is formed along the curved elastic portions.

The collection capacity of the liquid-absorbing article described in SE-C2,502,818 has thus been improved compared to similar articles of a more conventional type. This, has been achieved by arranging elastic members which extend with an essentially continuously curved portion across an area of the absorption body, the result of which is that the said elastic members are able to deform the article so that, during use, a cup-like or basin-like collection space is obtained for larger quantities of bodily excreta between the user and the liquid-absorbing article. The basin-like space has essentially no interruptions along the edge which delimits the basin space.

Although such an article, when it is being used, can be given a cup shape that is satisfactory for collecting liquid, this nevertheless requires a specific handling of the article. Thus, the cup shape has to be activated when applying the absorbent article, and it is important here to ensure that a cup really is formed, and not a raised hump, on that side of the article intended to be directed towards the user's body during use. Obtaining a correct shape of the absorbent article may, however, cause considerable difficulties for certain categories of user, for example people with impaired mobility in their hands or people with poor eyesight. There is therefore a risk of the known article, during use, assuming an incorrect shape which is not favourable for collecting liquid.

A further problem which arises when using absorbent articles is that the bodily fluids collected in the article come into contact with the user's skin and therefore cause skin irritation. As the absorbent article contains excrement, it may further be desirable to keep the excrement at a distance from the user's body, since this considerably facilitates the cleaning of the user's genital region when the article is to be changed.

Patent Specification WO 95/10993 thus already discloses a disposable diaper with an improved ability to keep bodily excreta away from the user's skin, comprising a sheet which protects the underclothes, a liquid-permeable surface material, an absorbent element placed between the protective sheet and the surface material, and a liquid-impermeable nonwoven covering which has an opening in the crotch area, the edge portions around the opening in the liquid-impermeable nonwoven covering forming sealing flaps around the opening.

For the diaper to be able to absorb bodily excreta more quickly, and to be able to retain this in a more efficient way, WO 95/10993 proposes that the absorbent element has an absorbent layer on which a diffusion layer is arranged, and that the dimensions of the opening in the nonwoven covering are smaller in the longitudinal and transverse directions than the corresponding dimensions of the diffusion layer. The disposable diaper described in WO 95/10993 is stated to comprise elastic means adjacent to the edges of the opening in the nonwoven covering, and along the longitudinal outer edges of the diaper.

Although such a known diaper, when compared to diapers with no nonwoven covering provided with an opening, has an improved ability to hold urine and excrement away from the user's skin, it is associated with certain disadvantages. For example, there is no guarantee, during use, of a liquid-receiving space forming between the liquid-impermeable nonwoven covering and the liquid-permeable surface material of the diaper. This means that during use of the diaper there is a risk of liquid instead flowing out across the surface of the liquid-impermeable nonwoven covering, with resultant leakage. The risk of such leakage is of course greatest, and has the most obvious consequences, when large amounts of bodily excreta are passed during a relatively short period of time. It can then happen that the small surface area of the liquid-permeable surface material which is exposed by the opening in the liquid-impermeable nonwoven covering is insufficient to be able to absorb the bodily excreta at the 'same rate as these impact the diaper.

Patent publications GB 2 265 550 B, GB 2 265 834 B and GB 2 266 055 A describe disposable diapers, or methods for producing these, in which use is made of an outer layer with an opening, arranged outside a conventional liquid-permeable surface layer on the,inside of the diaper. With the aid of elastic members, sealing flaps are formed in the outer layer, provided with the opening, which flaps are intended to provide a seal around the excretory organs of the user. Patent publication GB 2 265 550 A discloses elastic members which are arranged along and adjacent the edges of the opening in the outer layer, and thus elastizing the peripheri of the opening. Patent specification SE 504 062 C describes an absorbent article having an, elastic member arranged in direct contact with an absorption body. This absorbent article needs manipulation on application.

Despite the fact that strenuous efforts have thus long been made to improve the safety of absorbent articles against leakage, it has not been possible to reach a completely satisfactory solution to the leakage problem. Previously-known absorbent articles therefore only have a limited ability to locally collect and enclose large volumes of, for example, excrement and urine.

DESCRIPTION OF THE INVENTION

An object of the present invention is to provide a disposable liquid-absorbing article which is brought into a highly efficient collecting shape in the position of use. Another object of the invention is to provide a liquid-enclosing space which is created without the article needing to be manipulated on application, and which is retained during use of the absorbent article.

According to the invention, these aims are achieved in a particularly simple way through a combination of two different types of elastic systems which cooperate to produce a completely novel and especially advantageous elastic effect in an absorbent article.

An article designed according to the invention has a longitudinal direction and a transverse direction, a front portion, a rear portion and an intermediate crotch portion, and moreover two side edges extending in the longitudinal direction and two end edges extending in the transverse direction, and it comprises a liquid-permeable cover layer, a liquid-impermeable cover layer, and an absorption body enclosed between the two cover layers, and moreover a barrier layer, with at least one elastic member being arranged with prestressing in direct contact with the absorption body, and extending in an arched curve across the absorption body between the side edges of the article, and moreover that the barrier layer is arranged outside the liquid-permeable cover layer, the barrier layer partly covering the liquid-permeable cover layer and being anchored in the liquid-permeable cover layer only within areas of the barrier layer which are situated adjacent to the edges of the article, and that at least one elastic member is arranged in direct connection with the barrier layer, as a result of which the elastic member cooperates with the elastic member arranged in contact with the absorption body so as to form a constantly basin-shaped space between the barrier layer and the liquid-permeable cover layer.

By means of the invention it is possible to obtain a liquid-receiving space between a barrier layer, arranged across the liquid-permeable cover layer of an absorbent article, and the liquid-permeable cover layer. Elastic members arranged in the barrier layer activate elastic members which are fixed to the absorption body of the article and thereby initiate a shaping of the absorption body, so that the latter curves in the direction away from the barrier layer. In this way, the desired liquid-receiving space is obtained, and retained, without the user needing to manipulate the article prior to use.

A number of different combinations of design patterns of the elastic members can be used, both for the elastic members arranged in the barrier layer and for the elastic members fixed to the absorption body. The elastic members in the barrier layer can be arranged in straight and/or curved paths. In addition, the elastic members can extend in the longitudinal direction and/or transverse direction of the article. At least one elastic member in contact with the absorption body of the article must be arranged in an arch across the absorption body in order to obtain the desired basin-shaped space. It is advantageous, however, to combine two or more such curved elastic members in order to obtain wholly or partially closed basins in the article. For example, a forwardly curved elastic member and a rearwardly curved elastic member can together surround a basin-shaped area in the crotch portion of the article. In a corresponding way, it is possible to obtain a first closed area offset towards the front portion and intended for receiving urine, and a second closed area offset towards the rear and intended for receiving faeces. In addition, one or more curved elastic members can be combined with straight elastic members and with members having other functions. Examples of the latter type of elastic members are those which form leg elastic or waist elastic on diapers.

DESCRIPTION OF THE FIGURES

The invention will be described in greater detail hereinbelow with reference to the illustrative embodiments which are shown in the attached drawings, in which.

DESCRIPTION OF EMBODIMENTS

The illustrative embodiments chosen are incontinence protectors for collecting liquid and faeces from adults who, due to illness or age, suffer from severe incontinence symptoms.

Figure 1:
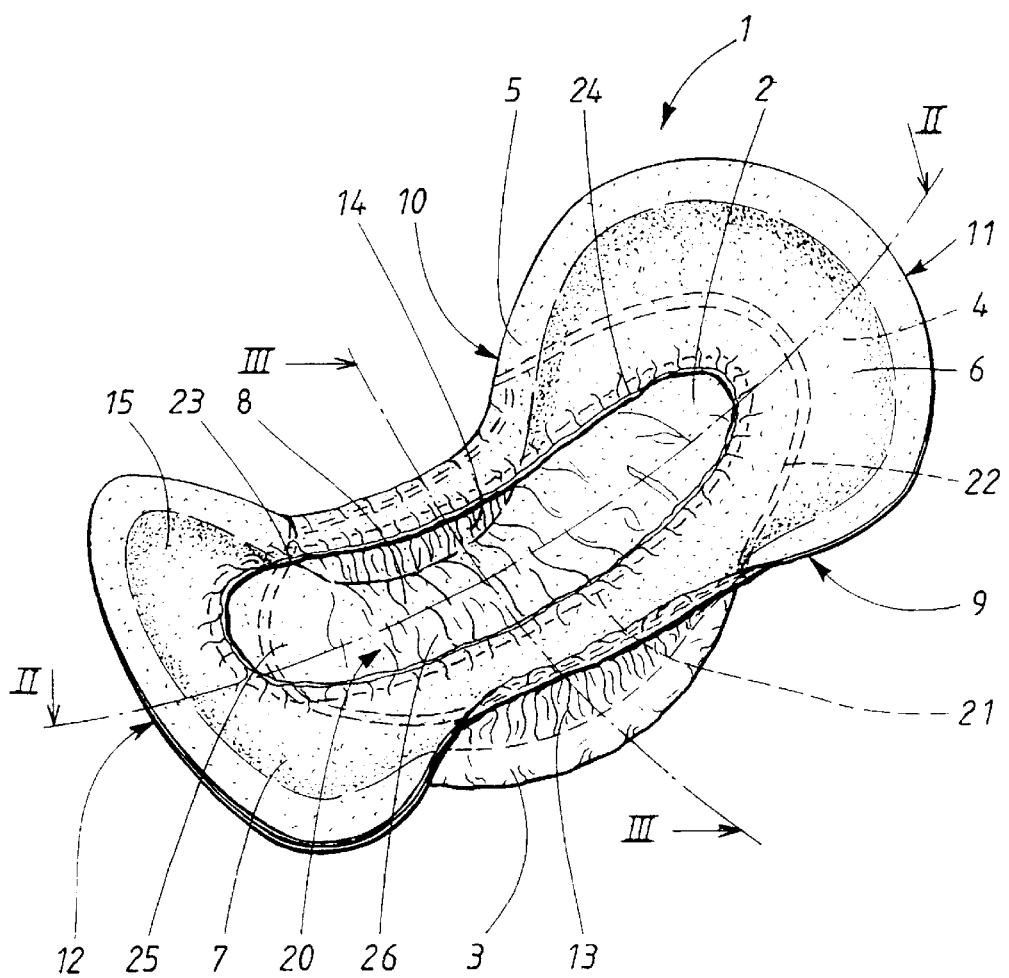
FIG. 1 is a perspective view of an incontinence protector according to a first embodiment of the invention.

The incontinence protector 1 shown in FIG. 1 comprises a liquid-permeable cover layer 2, arranged on that side of the incontinence protector 1 which is intended to be directed towards the user during use, a liquid-impermeable cover layer 3, arranged on that side of the incontinence protector 1 which is intended to be directed away from the user during use, and an absorption body 4 enclosed between the two cover layers 2, 3.

The material of the liquid-permeable cover layer 2 can be, for example, a perforated plastic film, a net of plastic or textile material, a nonwoven material, or a laminate of two or more such layers of material. The plastic materials which are used in the liquid-permeable surface material are usually thermoplastics, such as polyethylene or polypropylene. The term nonwoven material is intended to mean fibre fabrics which are not woven. Suitable nonwoven materials can consist of natural fibres, such as cellulose or cotton, or of synthetic fibres, such as polyethylene, polypropylene, polyester, polyurethane, nylon, or regenerated cellulose. It is also possible, of course, to use nonwoven materials made from fibres including two or more components, and mixtures of different fibre types.

The liquid-permeable cover layer 2 is intended to receive liquid and to transfer it into the absorption body 4. In addition, the cover layer 2 should be able to prevent so-called rewetting, that is to say absorbed bodily fluid penetrating back out from the absorption body 4.

The liquid-impermeable cover layer 3 consists of a liquid-impermeable material. Thin, liquid-impermeable plastic films are suitable for this purpose. It is also possible, however, to use materials which are initially liquid-permeable, but which have been provided with a coating of plastic, resin or other liquid-impermeable material. In this way, leakage of liquid from the underside of the absorbent article is prevented. The liquid-impermeable cover layer 3 can thus consist of any material which is compatible with the skin and which satisfies the criterion of liquid impermeability. Examples of materials which are suitable as blocking layers are plastic films, nonwoven materials and different types of laminates. Examples of plastic films that can be used are those which consist of poly-ethylene, polypropylene or polyester. Alternatively, the liquid-impermeable cover layer 3 can consist of a laminate of a liquid-impermeable plastic layer, directed towards the absorption body, and a nonwoven layer directed towards the user's underclothes. Such a structure affords a leakage-proof blocking layer with a textile feel.

The absorption body 4 can advantageously be made up essentially of cellulose fluff pulp. This can be present in the form of rolls, bales or sheets which are dry-defibred and converted in the fluffed form to a pulp mat, with or without admixture of so-called superabsorbents, which are polymers with the ability to absorb several times their own weight of water or body fluid. Examples of other materials that can be used are various types of natural fibres, such as cotton fibres, peat moss or the like. It is, of course, also possible to use absorbent synthetic fibres, or mixtures of natural fibres and synthetic fibres. The absorption material can further contain additional components such as liquid-diffusing members, or binders such as thermoplastic fibres which have been heat-treated in order to hold short fibres and particles together in a continuous unit. It is also possible to use different types of absorbent foam material in the absorption body 4. The absorption body 4 can consist of a continuous layer or can be made up of a number of different layers or parts. In addition, the absorption body 4 can be profiled, i.e. built up with different thicknesses in different areas of the incontinence protector.

The two cover layers 2, 3 are connected to each other outside the absorption body 4 and form a projecting margin 5 around the entire periphery of the incontinence protector 1. The cover layers 2, 3 can be joined together in any suitable way, such as by adhesive bonding, stitching, or welding with heat or ultrasound.

The incontinence protector 1 is slightly asymmetrical, but is essentially hourglass-shaped and in this connection has a front portion 6 which, during use, is intended to be directed towards the front on a user, a rear portion 7 which, during use, is intended to be directed towards the rear on a user, and an intermediate narrower crotch portion 8 intended to be arranged in the user's crotch region. Moreover, the incontinence protector 1 has two inwardly curved side edges 9, 10 and two outwardly curved end edges 11, 12. The absorption body 4 has approximately the same shape as the incontinence protector as a whole, but it has a slightly smaller planar extension. In particular, the absorption body 4 is narrower than the two cover layers 2, 3 at the crotch portion 8, as a result of which the cover layers 2, 3 form flexible edge portions 13, 14 on both sides of the absorption body 4 in the crotch portion 8.

The division of the incontinence protector 1 into two end portions 6, 7 and a crotch portion 8 must not be regarded as meaning that there are sharp boundaries between the various portions 6–8, but is primarily intended to facilitate the description of the incontinence protector 1, on the basis of the differences which exist between the various portions 6 to 8 in terms of how they are intended to be placed in relation to a user's body. Thus, the transition between the various portions 6 to 8 does not take place on defined transverse lines, but rather within diffuse transitional areas. The crotch portion 8 in this connection constitutes that part of the incontinence protector which, during use, is intended to receive and absorb most of the excreted body fluid.

A barrier layer 15 is arranged outside the liquid-permeable cover layer 2, on that side of the article which is intended to bear against the user's body. The barrier layer 15 has the same planar extension and shape as the liquid-permeable cover layer 2 and is fixed to the latter, by adhesive bonding, welding or the like, within the projecting cover margin 5.

The barrier layer 15 is expediently made of a thin, easily bendable and skin-compatible layer material. The materials and material laminates which have been mentioned in connection with the two cover layers can thus be used. The barrier layer 15 advantageously has a certain ability to withstand liquid penetration, as a result of which liquid which has collected inside of the layer 15, between this and the liquid-permeable cover layer 2, is prevented from penetrating out through the layer. It is an advantage, however, if the barrier layer 15 is breathable and lets through vapour and gases.

Figure 3:
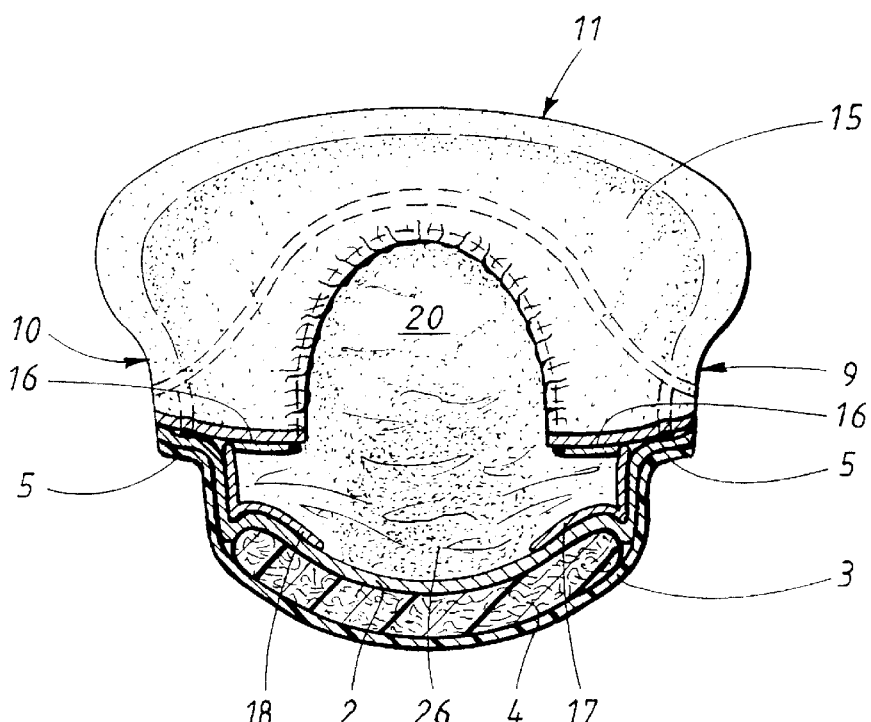
FIG. 3 is a cross-section, along the line III—III, through the incontinence protector in FIG. 1.

FIG. 3 shows that the inside 16 of the barrier layer 15, directed towards the liquid-permeable cover layer 2, and also an edge portion 17, 18 of the liquid-permeable cover layer 2 along each side edge 9, 10 of the incontinence protector 1, are treated with a liquid-repellent agent in order to increase the safety against leakage. Examples of liquid-repellent agent that can be used are thin coatings of plastic, wax or the like. Alternatively, a layer of hydrophobic non-woven material or plastic film can be arranged across the material surfaces 16–18 which it is desired to render liquid-repellent. It is also possible to start from a material which is initially liquid-repellent and to then treat those parts of the barrier layer 15 and the liquid-permeable cover layer 2 which are to be more hydrophilic with surfactants or other surface-active substances or treatments. A further possibility is to use zoned nonwoven material, i.e. nonwoven material which, because of differing material composition or treatment, has, right from the outset, different liquid permeability within different areas 2.

According to one embodiment which is not shown, the barrier layer 15 can alternatively consist of a three-dimensionally perforated plastic film which lets liquid through in only one direction. It is thereby possible to obtain a barrier layer 15 which is able to let in liquid impacting the barrier layer 15, without the liquid then being able to pass out again through the layer 15.

The barrier layer 15 is provided with a through-opening 20 via which liquid can pass into the incontinence protector 1. Running around the opening there is an elastic member 21 which is intended to draw the edges of the opening 20 together so that these are lifted up from the liquid-permeable cover layer 2. The elastic member 21 also serves to create a flexible seal between the barrier layer 15 and the user's body. The contraction of the material around the opening 20 is achieved by the fact that the elastic member 21 is prestressed. The prestressing can be obtained by means of the elastic member 21 being stretched out and fixed to the barrier layer 15 in the stretched state. Alternatively, the elastic member 21 can consist of a material whose elastic contractibility is activated after arrangement on the barrier layer 15. Such activation can take place, for example, by heating or with infrared radiation.

In addition, elastic members 22, 23 are arranged in connection with the absorption body 4. Here, a first elastic member 22 is arranged across the front portion 6 of the incontinence protector, between the liquid-permeable cover layer 2 and the absorption body 4. The first elastic member 22 extends in an arch, direct towards the front edge 11, between the side edges 9, 10 of the incontinence protector. In a corresponding manner, a second elastic member 23 is arranged across the rear portion 7, in an arch towards the rear edge 12. The second elastic member 23 extends between the absorption body 4 and the liquid-permeable cover layer 2 and further out into the projecting cover margin 5 on both sides of the absorption body 4 in the crotch portion 8. Those parts of the second elastic member 23 which are arranged in the projecting cover margin 5 thus form the leg elastics of the incontinence protector.

The elastic members 22, 23 are arranged in direct contact with the absorption body 4 in such a way that contraction of the elastic members 22, 23 also causes contraction of the absorption body 4.

In the example shown, the elastic members are connected to the liquid-permeable layer 2, on the inside thereof, i.e. between the absorption body 12 and the cover layer 2, but they can of course alternatively be arranged on the outside of the layer. According to a further alternative embodiment, the elastic members 22, 23 can be arranged between the liquid-impermeable cover layer 3 and the absorption body.

The elastic members 21, 22, 23 consist, for example, of one or more strings or bands of elastic material, such as rubber, polyurethane, elastic nonwoven, or the like. The elastic members can be covered with a spun-on thread casing which makes it easier for the elastic members to be joined by adhesive binder to components in the incontinence protector. In addition, such a thread casing permits elastic movements in the elastic core. The elastic members 22, 23 tend to be drawn together and the elastic strings or bands are for this purpose prestressed, i.e. stretched to a certain extent before they have been anchored in the incontinence protector. They are anchored, for example, by means of adhesive binder which is arranged along certain sections of the elastic or along its whole extent. The elastic members 22, 23 are preferably anchored both to the liquid-permeable cover layer 2 and to the absorption body 4.

According to one alternative embodiment, the elastic member 21 fixed to the barrier layer can be omitted. In this case, a completely or partially elastic barrier layer can be used instead.

By means of the contracting action of the curved elastic, and by means of its anchoring in the one cover layer 2, and the connection of the layer to the absorption body 4, said absorption body 4 can be deformed so that raised front and rear basin walls 24, 25 are formed in relation to the comparatively planar inner surface of the crotch portion 8. Correspondingly, the flexible cover flaps 13, 14 constitute basin walls on the side edges 9, 10 of the incontinence protector, the basin walls 13, 14, 24, 25 together enclosing a basin-like space 26.

The shaping of the basin-like space 26 is activated by the elastic member 21 arranged around the opening 20 in the barrier layer 15. It is by means of the contracting force in the elastic member 21 in the barrier layer 15 that the incontinence protector is in fact made to curve in both the longitudinal direction and the transverse direction. Thus, by means of the contraction of the elastic members 22, 23 arranged in contact with the absorption body 4, a constant cup-shaped space is necessarily formed between the barrier layer 15 and the liquid-permeable cover layer 2. By arranging an elastic member 21 in a special layer 15 which is arranged outside the liquid-permeable cover layer 2, and which is only fixed to the liquid-permeable cover layer 2 within delimited areas at the edges 9–12 of the incontinence protector, a contraction of the incontinence protector takes place on that surface which is intended to be directed towards the user during use. This means that the curvature of the absorption body 4 under the effect of the contracting forces in the barrier layer 15 will necessarily take place in the opposite direction, i.e. in the direction away from the surface directed towards the user during use. In this way, a cup directed towards the user is automatically formed, and not a raised mound, without any manipulation whatsoever of the incontinence protector being needed when applying it.

The shaping effect exerted by the elastic members 21–23 will be explained in more detail below. The elastic members arranged in contact with the absorption body exert their shaping effect by means of the fact that the elastic is contractile and thus strives to reduce its length. By means of the elastic being anchored in the liquid-permeable cover layer 2, the latter is entrained in the contracting movement of the elastic. The liquid-permeable cover layer 2 is, in turn, connected via its surface to the absorption body 4, as a result of which pulling forces in the plane of the cover layer 2 are transmitted to the absorption body 4. Due to the elastic having been laid in a curved configuration over the greater part of its extent across the absorption body 4, the contracting effect means that the elastic at each point over the curved extent applies a component force which is directed towards the corresponding centre of curvature of the curved portion at each point. If the curved portions have varying radii of curvature, there are different centres of curvature for each separate point. The absorption body 4 is relatively flexible together with the cover 2, 3, but still exhibits a certain resistance to compression. These properties mean that the torsional moments caused by the forces in the elastic members 22, 23 bring about a deformation of the incontinence protector and permit the appearance of the front and rear basin walls 24, 25 in the areas with curved elastic. The inherent stiffness of the incontinence protector is such that it is not deformed from its flat state simply by the effect of the elastic members 22, 23 arranged in contact with the absorption body. Instead, the sought deformation is initiated by the effect of the elastic member 21 arranged in the barrier layer 15.

Figure 2:
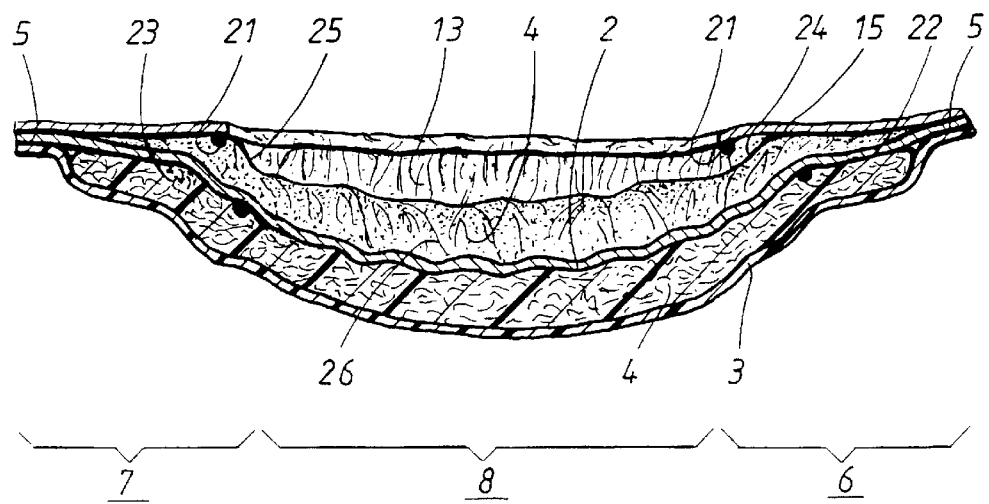
FIG. 2 is a longitudinal section, along the line II—II, through the incontinence protector in FIG. 1.
Figure 4:
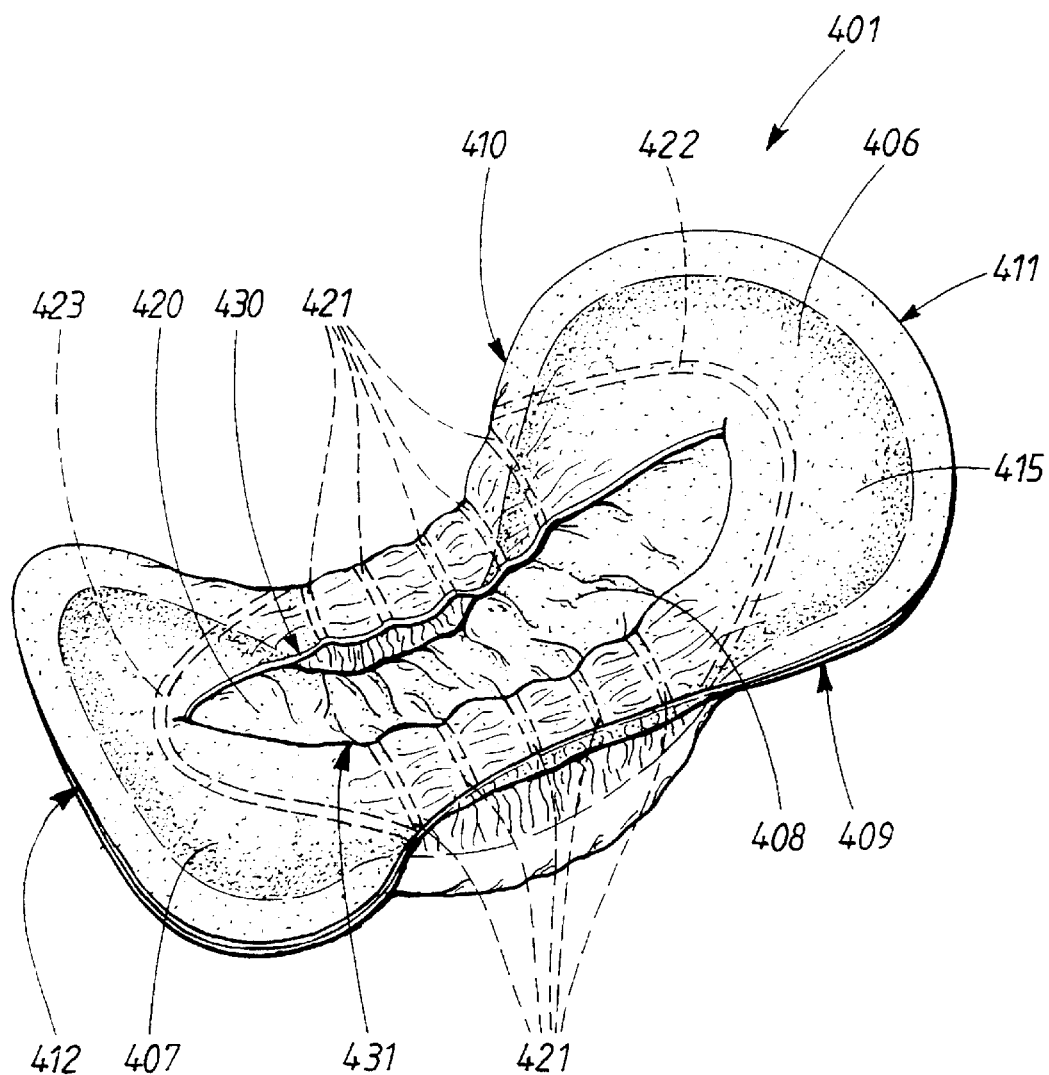
FIG. 4 is a perspective view of an incontinence protector according to a second embodiment of the invention.

FIG. 4 shows an incontinence protector 401 of the same basic structure as the incontinence protector 1 shown in FIGS. 1–3. The main difference is that the barrier layer 415 has a longitudinal opening 420 which is formed by arranging a slit through the barrier layer 415. In order to widen the slit to an opening 420 having an extension in the transverse direction of the incontinence protector 401, elastic members 421 are arranged on the barrier layer 415. The elastic members 421 extend on both sides of the slit, at right angles thereto, between the side edges 409, 410 of the incontinence protector and the edges 430, 431 of the slit. In an alternative embodiment (not shown), the transverse elastic members 421 are combined with longitudinal elastic members arranged along the edges 430, 431 of the slit at the front and/or rear portion 406, 407 of the incontinence protector.

As with the incontinence protector 1 shown in FIGS. 1–3, elastic members 422, 423 are arranged in a curved shape across the front and rear portions 406, 407 of the incontinence protector. A difference here is that the rear elastic member 423 extends only over the absorption body 404 and does not therefore form longitudinal elastic along the side edges 409, 410 of the incontinence protector 401.

Figure 7:
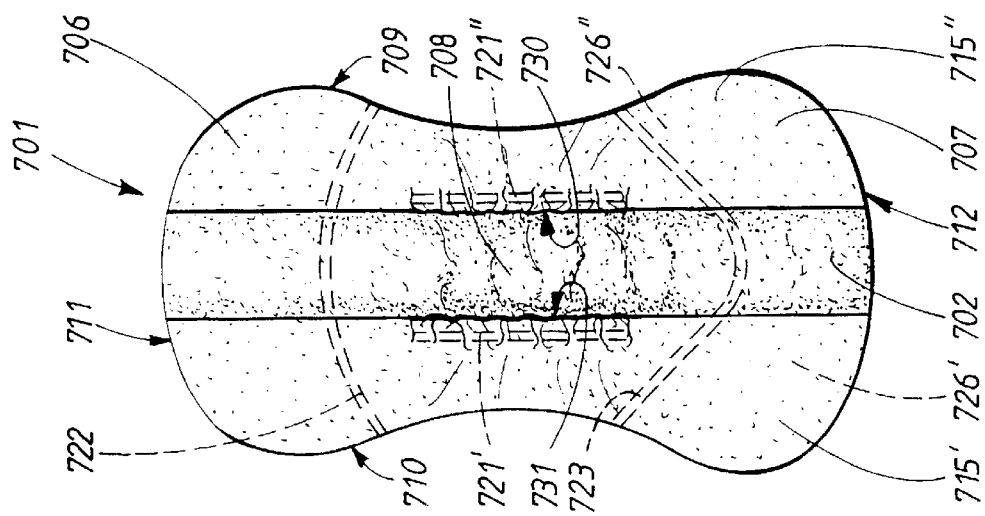
FIGS. 5 to 7 show incontinence protectors according to further embodiments of the invention.
Figure 6:
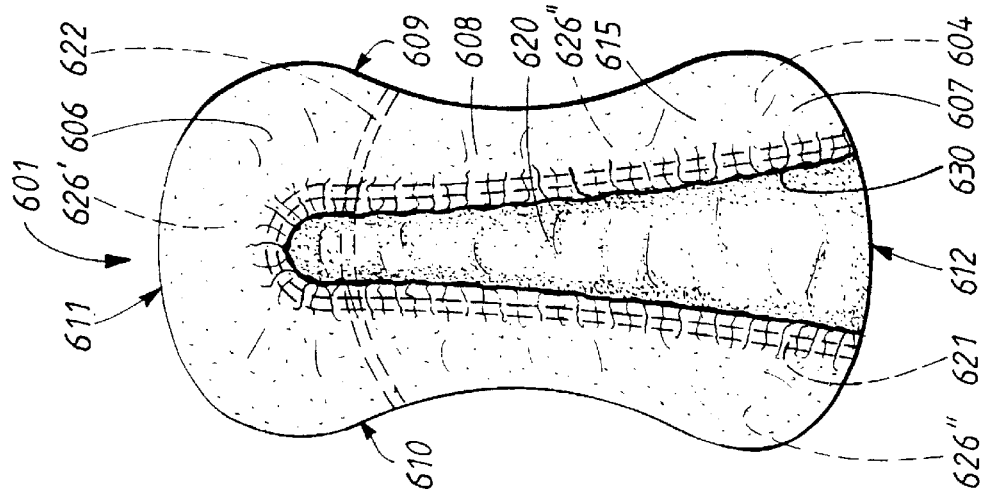
Figure 5:
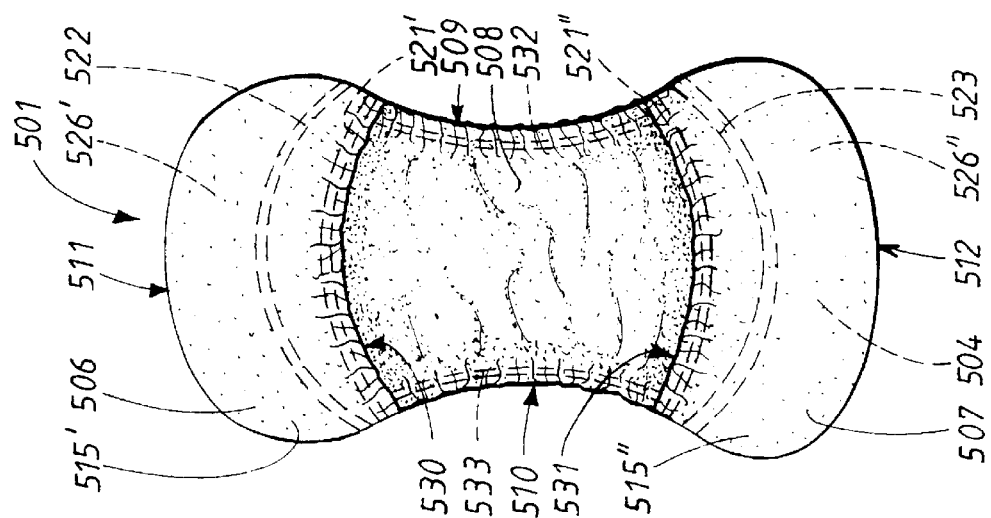

Further alternative illustrative embodiments are shown in FIGS. 5–7. The incontinence protector 501 shown in FIG. 5 has a two-part barrier layer 515', 515", forming liquid-receiving pockets 526', 526" at the front and rear portions 506, 507, respectively, of the incontinence protector 501. Elastic members 521', 521" are arranged along the free edges 530, 531 on the barrier layer parts 515', 515". Elastic members 522, 523 are arranged in contact with the absorption body 504 and run in an arch shape over the front and rear portions 506, 507. Elastic members 532, 533 are also arranged along the longitudinal side edges 509, 510 of the incontinence protector at the crotch portion 508.

The incontinence protector 601 shown in FIG. 6 has a barrier layer 615 with a cutout portion 620 which extends from the rear edge 612 of the incontinence protector in the direction towards the front edge 611 and ends in a rounded point in the front portion 606 of the incontinence protector. In this way a liquid-receiving pocket 626' is formed in the front portion 606 and liquid-receiving spaces 626" are formed under the barrier layer 615 along the side edges 609, 610.

An elastic member 621 is arranged in a continuous loop which adjoins the edge 630 of the cutout portion 620. Alternatively, the elastic member 621 can of course be divided into two separate straight segments arranged on each side of the cutout 620. An elastic member 622 is arranged in an arch curving towards the front edge 611, between the side edges 609, 610 of the incontinence protector, in direct contact with the absorption body 604. As has been described in connection with FIGS. 1–5, it is of course also possible, in a corresponding manner, to arrange one or more curved elastic members on the rear portion 607 of the incontinence protector.

The incontinence protector 701 shown in FIG. 7 has a barrier layer comprising two parts 715', 715" extending in the longitudinal direction of the incontinence protector 701. The barrier layer parts 715', 715" are fixed to the incontinence protector along those portions which coincide with the side edges 709, 710 and the end edges 711, 7.12. In this way, liquid-receiving side pockets 726', 726" are formed between the barrier layer parts 715', 715" and the liquid-permeable cover layer 702 of the incontinence protector. Elastic members 721', 721" are arranged along the free edges 730, 731 on the barrier flaps 715, 715" in the crotch portion 708 of the incontinence protector. Curved elastic members 722, 723 are arranged in direct contact with the absorption body 704 in the front portion 706 and rear portion 707, respectively, of the incontinence protector. The elastic members 721', 721", 722, 723 cooperate to shape the incontinence protector and to create a constant liquid-receiving space between the barrier layer parts 715', 715" and the liquid-permeable cover layer 702 during use.

The incontinence protector 701 shown in FIG. 7 can advantageously also be provided with a barrier flap (not shown) arranged in one or both of the end portions 706, 707. Such barrier flaps increase the security against leakage at the front and rear of the incontinence protector and can be provided with elastic members. The incontinence protector shown in FIG. 6 can also be combined in a corresponding manner with a transverse rear leakage barrier flap.

The invention must not be regarded as being limited to the illustrative embodiments described above and shown in the drawings, and instead a number of further variants and modifications are possible within the scope of the attached patent claims. In particular, it is possible to arrange elastic members in one or more barrier layers in a number of ways other than those that have been described. It is likewise possible for the curved elastic members arranged in contact with the absorption body to be combined with further elastic members, for example in order to obtain leg elastic, or waist elastic, on a diaper. It will be appreciated that the illustrative embodiments which have been described can be combined with each other, as long as at least one elastic member is arranged in a barrier layer of an absorbent article and as long as the article has a curved elastic member which is arranged in contact with the absorption body of the article and which is activated by the contraction in the elastic member arranged in the barrier layer.

In order to simplify the description of the invention, the illustrative embodiments have focused exclusively on incontinence protectors. However, it is self-evident that the invention can be used equally well to improve the leakage security of a diaper or a sanitary towel. In addition, fastening arrangements and the like, which are not of importance for the invention, have been omitted from the description.

What is claimed is:

1. An absorbent article having a longitudinal direction and a transverse direction and having a front portion, a rear portion and an intermediate crotch portion, and moreover having two side edges extending in the longitudinal direction and two end edges extending in the transverse direction, and comprising a liquid-permeable cover layer, a liquid-impermeable cover layer and an absorption body enclosed between the two cover layers, and moreover comprising a barrier layer, with at least one absorption body elastic member being arranged with prestressing anchored to the absorption body, and extending in an arched curve across the absorption body from one of the side edges to another of the side edges of the article, and moreover that the barrier layer is arranged outside the liquid-permeable cover layer, the barrier layer partly covering the liquid-permeable cover layer and being anchored in the liquid-permeable cover layer only within areas of the barrier layer which are situated along the edges of the article, and that at least one barrier layer elastic member is arranged in direct connection with the barrier layer, as a result of which the barrier layer elastic member cooperates with the absorption body elastic member arranged in contact with the absorption body so as to form a constantly basin-shaped space between the barrier layer and the liquid-permeable cover layer.

2. An article according to claim 1, wherein the absorption body elastic member arranged in contact with the absorption body is arranged in the front portion of the article and extends in a curved arch directed towards the front edge of the article.

3. An article according to claim 1, wherein the absorption body elastic member arranged in contact with the absorption body is arranged in the rear portion of the article and runs in a curved arch directed towards the rear edge of the article.

4. An article according to claim 1, further comprising a second absorption body elastic member arranged in the rear portion of the article and runs in a curved arch towards the rear edge of the article, said curved absorption body elastic members together forming an essentially closed perimeter around a cup-shaped space between the liquid-permeable cover layer and the barrier layer.

5. An article according to claim 4, wherein the absorption body elastic members are arranged along at least portions of the side edges of the article.

6. An article according to claim 5, wherein the absorption body narrows in the crotch portion so that the cover layers form flexible flaps outside the absorption body at the crotch portion, and the flexible flaps, under the influence of the absorption body elastic members arranged along the side edges, form raised basin walls on both sides of the absorption body.

7. An article according to claim 1 in which the absorption body is essentially made of cellulose fluff pulp.

8. An article according to claim 1 wherein the absorption material comprises superabsorbent material.

9. An article according to claim 1 in which the absorption material comprises a foam.

10. An article according to claim 1 wherein curved elastic members are arranged to form a first closed area offset towards the front portion and intended for receiving urine, and to form a second closed area offset towards the rear portion and intended for receiving faeces.

11. An article according to claim 1, wherein the barrier layer has essentially the same planar extension as the article itself and is fixed to the liquid-permeable cover layer along the side edges of the article and also along its end edges, and the barrier layer has an elongate opening extending in the longitudinal direction of the article.

12. An article according to claim 11, wherein there are two barrier layer elastic members extending in the transverse direction arranged on both sides of the opening.

13. An article according to claim 1, wherein the barrier layer is arranged as a pocket on at least one end portion of the article.

14. An article according to claim 1, wherein the barrier layer comprises two parts arranged in the longitudinal direction of the article, along the longitudinal side edges of the article.

15. An article according to claim 1, wherein the barrier layer has at least one area which is treated with means for reducing the liquid permeability.

16. An article according to claim 1, in which the liquid-permeable cover layer has at least one area which is treated with means for reducing the liquid permeability.

* * * * *